United States Patent [19]

Kolff et al.

[11] Patent Number: 5,306,295
[45] Date of Patent: Apr. 26, 1994

[54] ELECTROHYDRAULIC HEART WITH SEPTUM MOUNTED PUMP

[75] Inventors: Willem J. Kolff; Stephen R. Topaz, both of Salt Lake City, Utah; Peter A. Topaz, West Lafayette, Ind.; N. Dan Bishop; Dmitry M. Golub, both of Salt Lake City, Utah; Long S. Yu, Andover, Mass.; Yvo Smulders; Mark Stegeman, both of Amsterdam, Netherlands; Cornelis Verhoef, Brandwijk, Netherlands

[73] Assignee: University of Utah Research Foundation, Salt Lake City, Utah

[21] Appl. No.: 876,387

[22] Filed: Apr. 30, 1992

[51] Int. Cl.$^5$ .................................. A61M 1/12
[52] U.S. Cl. ........................................ 623/3; 417/412
[58] Field of Search .............................. 623/3; 600/16; 417/413 R, 412

[56] References Cited

U.S. PATENT DOCUMENTS

| 3,842,440 | 10/1974 | Karlson | 623/3 |
| 3,874,002 | 4/1975 | Kurparek | 623/3 |
| 4,173,796 | 11/1979 | Jarvik | 623/3 |
| 4,524,466 | 6/1985 | Hall et al. | 623/3 |
| 4,750,903 | 6/1988 | Cheng | 623/3 |

OTHER PUBLICATIONS

Nosé et al., "Experimental Results for Chronic Left Ventricular Assist and Total Artificial Heart Development", Artificial Organs, 7(1), 55–63, 1983.

Primary Examiner—Randall L. Green
Assistant Examiner—D. Willse
Attorney, Agent, or Firm—Thorpe, North & Western

[57] ABSTRACT

A total artificial heart for placement inside a living body comprising right and left ventricle enclosures, wherein each ventricle includes an exterior wall formed of (i) contacting wall structure and (ii) noncontacting wall structure which collectively enclose an interior volume comprised of a blood chamber and a pumping chamber. The contacting wall structure of each ventricle enclosure is configured for intercontacting relationship wherein the contacting walls of the respective ventricles form a septum which structurally separates the interior volume of the right ventricle from the interior volume of the left ventricle. The noncontacting wall structure comprises the remaining exterior wall of each ventricle enclosure. A fluid drive motor capable of reversible flow is positioned within and circumscribed by the septum and includes a flow channel therethrough which communicates between the respective pumping chambers of the right and left ventricle enclosures. A pumping fluid is contained within the pumping chambers and is responsive to the fluid drive motor to be reversibly transferred between the pumping chambers of the right and left ventricle to enlarge and contract the blood chamber and thereby simulate natural pumping action of the heart.

14 Claims, 5 Drawing Sheets

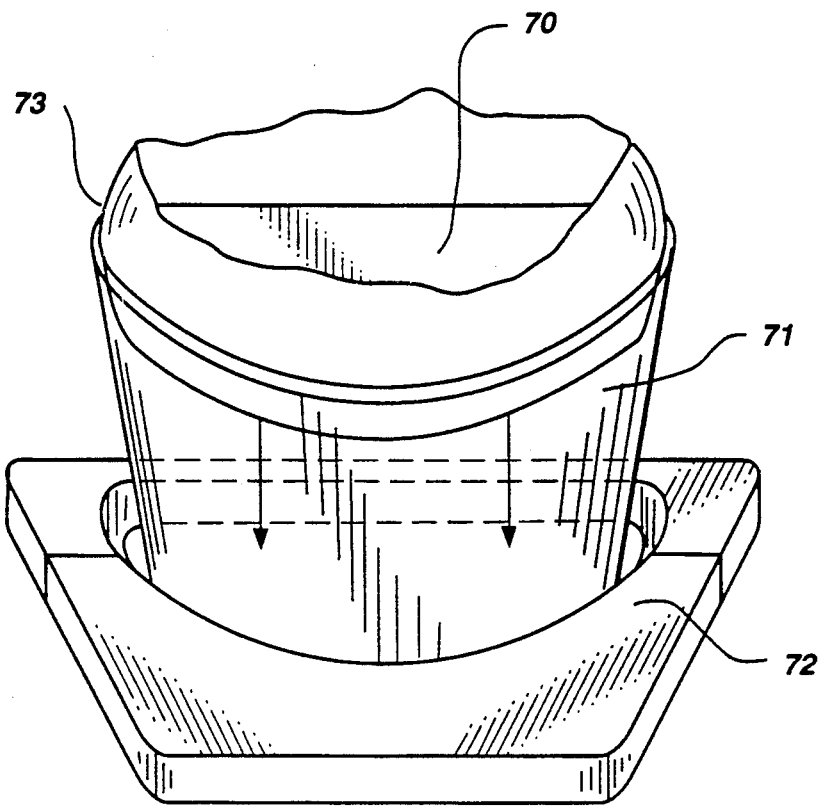
*Fig. 8*
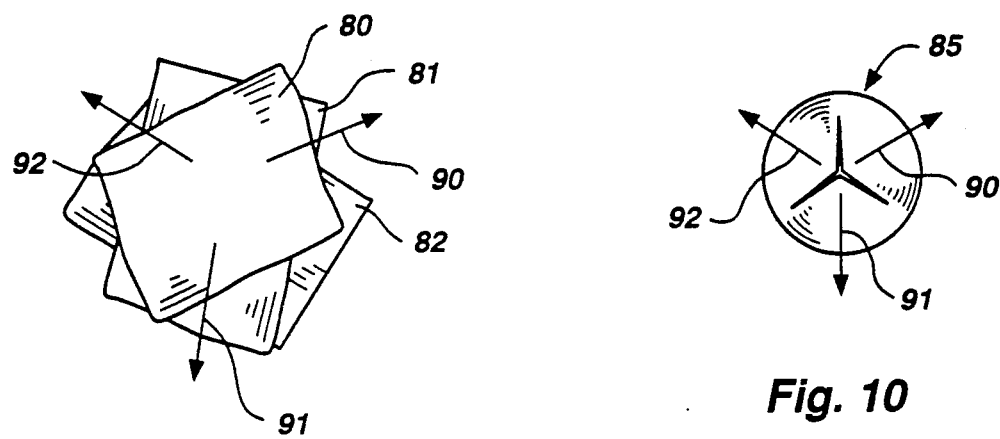
*Fig. 9*  *Fig. 10*

ELECTROHYDRAULIC HEART WITH SEPTUM MOUNTED PUMP

This work was supported in part by NIH Grant 2-RO1-HL-38304 from the National Heart, Lung and Blood Institute of the National Institutes of Health and by contributions made to Dr. Willem J. Kolff's Development Fund.

BACKGROUND OF THE INVENTION

1. Field of the Invention

This invention pertains to total artificial hearts (TAH) which are self contained for permanent emplacement within a living being for total replacement of a natural heart. More particularly, this invention relates to a TAH which utilizes a hydraulic pumping system with a small, reversible pump to actuate pumping action.

2. Prior Art

Despite the climbing mortality rate of persons who die annually because of the limited supply of heart transplants, there are currently no commercial artificial hearts available for patient use. It is estimated that 35,000 people per year in the United States alone need a replacement for the irreparable natural heart. Because only 2,000 donor hearts are available on the average, the vast majority (33,000) of these heart patients will die. By 1995, it is estimated that the target population for circulation support devices will be 60,300. *Artificial Heart*, Institute of Medicine, Jul. 23, 1991 (advance copy).

Numerous patents have been issued which offer various technologies intended to address this critical need. These technologies extend from ventricle assist devices to the fully self contained TAH. U.S. Pat. No. 4,173,796 issued to the present applicant in 1979 introduced the concept of a permanent electrohydraulic heart capable of being implanted within a living body with pumping support being provided by a reversible, electric impeller motor. The theory of operation for this device was to place the motor at the base of the TAH and reversibly transfer hydraulic pumping fluid between respective pumping chambers of the left and right ventricles. The motor was situated below the blood chambers and was separated by means of channels.

Current commercial artificial heart devices are limited to air driven hearts whose cost approaches $100,000 per TAH and supporting air drive system, not counting associated medical fees for emplacement. Because of this high cost, each consideration of use of a TAH remains primarily a financial issue. Until such costs can be contained, it is apparent that artificial hearts will remain a theoretical solution to a real life problem.

Numerous problems encumbered the intended success of the electrohydraulic heart invented by Jarvik and issued to the present applicant in the patent referenced above. The capacity of the motor was limited by its conventional design. Such design features included the concept of a central rotating shaft with attached impeller blades radiating outward from this shaft. The shaft was rotated by a brushless DC motor in a conventional manner. Fluid flow was advanced through an annular channel in a reversible manner, based on the direction of shaft rotation.

Response time of the hydraulic fluid was not optimal. This was perhaps a byproduct of several design features. For example, the annular channel configuration imposed a substantial amount of surface area and frictional drag on the transferring fluid between pumping chambers of the respective ventricles. In addition to the drag induced by the large surface area of the flow channel within the motor, there was further drag developed by the substantial distance of travel required of the fluid as it moved from one pumping chamber to the other. This was a byproduct of the placement of the pump below the pumping chambers providing a flow channel to direct the flow between the left and right ventricles. Separate wall structure was provided below the septum to isolate the pump motor and define the described flow channel. Such a tortuous path for fluid movement which is being directionally reversed as much as 120 times per minute posed a major obstacle to confidence in the long term survivability of the TAH.

What is needed is a greatly simplified hydraulic fluid transfer system which optimizes rates of fluid transfer and minimizes drag, without perpetuating the former high cost of production and emplacement.

OBJECTS AND SUMMARY OF THE INVENTION

It is an object of the present invention to provide a TAH which can be permanently implanted within a living body and capable of meeting the demands of blood circulation by simulation of pumping action provided by a natural heart.

It is a further object of this invention to provide a TAH which is powered by an electrohydraulic fluid transfer system which minimizes the drag applied to the transferring fluid which reciprocates between the pumping chambers of the respective ventricles.

A still further object of this invention is to minimize the fluid path displacement distance required of the reciprocating fluid, thereby maximizing work output of the drive motor.

Yet another object of this invention is to provide a fluid drive motor which minimizes applied drag to the transferring fluid, as well as providing reduced wear to motor components.

Other objects include the enhancement of valve components within the TAH for increasing flow efficiencies and improving blood compatibility of blood chambers by improving the seamless character of structural junctures of internal compartments within the TAH. Yet another object of the invention is to present a safeguard to excessive suction by providing an inward collapsible (but not distensible) wall section of the ventricle to compensate for the lessor cardiac output of the right ventricle compared the left.

These and other objects are realized in a total artificial heart (TAH) for placement inside a living body, which comprises first and second ventricle enclosures operable as left and right ventricles, each ventricle enclosure having an exterior wall formed of (i) contacting wall structure and (ii) noncontacting wall structure which collectively encloses an interior volume comprised of a blood chamber and pumping chamber. The interior volume includes at least one pumping membrane sealed at an interior surface of the exterior wall and is configured to divide the blood chamber from the pumping chamber. The contacting wall structure of each ventricle enclosure is configured for intercontacting relationship wherein the contacting walls of the respective ventricles form a septum which structurally separates the interior volume of the first ventricle enclosure from the interior volume of the second ventricle enclosure. The noncontacting wall structure comprises the remaining exterior wall of each ventricle enclosure. Part of this non contacting wall chamber is soft and flexible but practically non distensible. If for some reason a pressure is generated inside the left ventricle which is lower than the environmental pressure inside the chest, then this part of the wall buckles in, thereby eliminating excessive suction which when transferred to the atrium might suck in the atrial wall which might occlude the aperture of the in flow valve.

The pumping chamber of each ventricle is collectively enclosed by (i) at least a portion of the septum, (ii) the pumping membrane and (iii) any surrounding noncontacting wall structure. The blood chamber is enclosed by the pumping membrane on one side and the remaining exterior wall which is joined to the pumping membrane. Each blood chamber is provided with valved inlet and outlet means suitable for use in a TAH to enable unidirectional flow of blood through each ventricle in response to pumping action of the pumping membrane. A fluid drive motor capable of reversible flow is positioned within and circumscribed by the septum and includes a flow channel therethrough which communicates directly between the respective pumping chambers of the left and right ventricle enclosures. This improved position of the drive motor within the septum reduces the displacement distance of the reciprocating drive fluid, as well as drag forces attending such displacement. The result is a greatly enhanced efficiency which is complemented by a significant reduction in design complexity and attendant cost.

Other design features include improved motor dynamics by elimination of a central drive shaft and enhanced flow rates through the drive motor, as well as improving valve design for unidirectional blood flow. Alternatively, a motor design with a central shaft may be used with the motor in the center and the impeller blades situated around the motor. Improved blood compatibility is achieved with new techniques of radio-frequency welding of polymer junctions in accordance with methods disclosed herein which enhance the seamless character of such junctures.

Other objects and features will be apparent to those skilled in the art, based on the following detailed description, taken in combination with the accompanying drawings.

DESCRIPTION OF THE DRAWINGS

FIG. 8 depicts a device for radio frequency welding of polymer seams within a TAH in accordance with the described invention.

FIG. 9 shows preorientation of polymer sheets to be thermo formed into a tricusp semilunar valve.

FIG. 10 illustrates a tricusp semilunar valve formed from the sheets of polymer shown in FIG. 9.

DETAILED DESCRIPTION OF THE INVENTION

Figure 1:
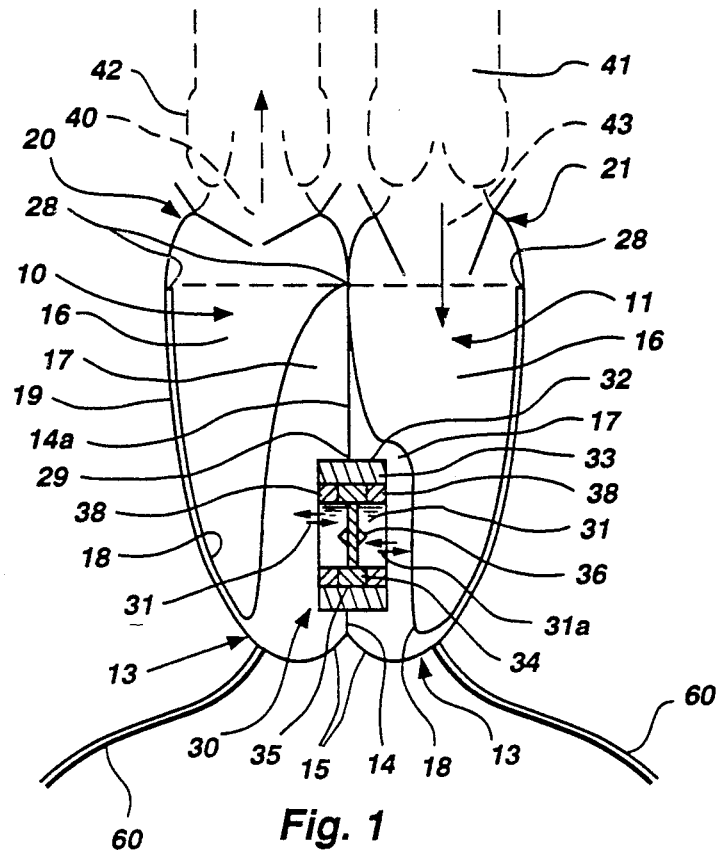
FIG. 1 is a graphic representation in cross section of a total artificial heart embodying the present invention.

FIG. 1 depicts a TAH having ventricle enclosures 10 and 11 operable as left and right ventricles in the TAH. Each ventricle enclosure has an exterior wall 13 formed of (i) contacting wall structure 14 and (ii) noncontacting wall structure 15, which collectively encloses an interior volume comprised of a blood chamber 16 and pumping chamber 17. This interior volume includes at least one pumping membrane 18 which is sealed at an interior surface 19 of the exterior wall 13 and is configured to divide said blood chamber 16 from said pumping chamber 17.

The contacting wall structure 14 of each ventricle enclosure is configured for intercontacting relationship wherein the two contacting walls 14 form a single septum 14a which structurally separates the interior volume of the left ventricle enclosure from the interior volume of the right ventricle enclosure. Reference to contacting walls is accordingly intended to generally refer to the position where walls of the left and right ventricle join to form an opening 29 into which the drive motor is mounted. Although this septum has been described as the cooperation of two separate contacting walls 14, it could function equally well with a single wall of one of the ventricles which is sealed to the other ventricle, forming a common wall which could serve as the septum 14a. Therefore, as used herein, contacting walls may refer to a single, common wall which serves as a contacting wall from each attached ventricle enclosure, as well as the union of two separate walls in intercontacting relationship. As will be shown hereafter, the primary function of this septum from a perspective of the present invention is to physically support a fluid drive motor 30 which provides a flow path directly between the respective pumping chambers, thereby avoiding the need to channel pumping fluid around the septum.

The noncontacting wall structure 15 generally refers to the remaining exterior wall of each ventricle enclosure. This includes the snout 20 and 21 of each ventricle, as well as the remaining wall structure which is not forming part of the septum 14a.

It will be noted that the pumping chamber 17 of each ventricle is enclosed by at least a portion of the septum 14a, along with the pumping membrane and any surrounding noncontacting wall structure. This chamber contains the pumping fluid, which may be an hydraulic fluid such as water, saline or methyl silicone. In accordance with conventional practice, the pumping fluid is forced between the respective pumping chambers of the left and right ventricles to alternately increase and decrease the volume of the blood chambers 16, thereby simulating the natural pumping action of a heart.

The blood chamber 16 is enclosed by the pumping membrane on one side and the remaining exterior wall which is joined to the pumping membrane at juncture 28. In the illustrated embodiment, the blood chamber is actually contained within a sac-type structure which is inserted into the exterior wall of the ventricle which operates as a housing. The blood sac is a polyurethane composition formed of one or more layers of polyurethane. A particular embodiment was formed of two layers of 0.020 inches thickness of Pellethane which were thermo formed or molded over a mandrel. The resulting layers are 0.012 inches thick and are lubricated therebetween with graphite. It has been found that the flex life of two separated layers is greater than that of a single layer of heavier polyurethane. Other elastomers such as silicones may also be used. It can be seen from the right ventricle of FIG. 1 that the blood sac or chamber is sized to substantially fill the interior volume of the ventricle in diastole before the pumping fluid is forced to the opposing pumping chamber. It can also be seen that the blood sac or chamber is generally suspended within the pumping chamber, such as is illustrated by the left ventricle in FIG. 1. It is preferred to attach the outside wall 18 of the blood sac to the inside of the outer wall 13 of the pumping chamber.

Figure 3:
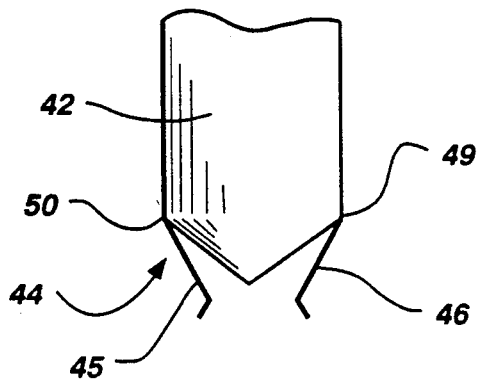
FIG. 3 graphically illustrates a bileaflet valve used in connection with the disclosed TAH.
Figure 4:
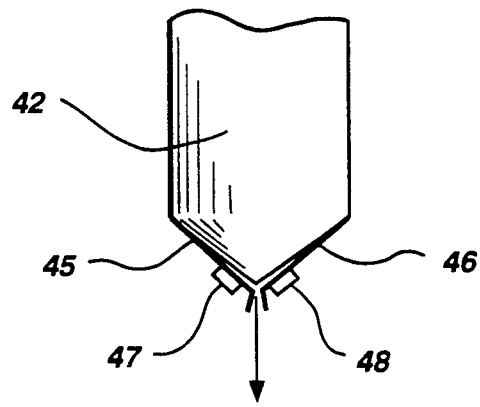
FIG. 4 shows the bileaflet valve of FIG. 3 modified with magnets of common polarity for urging the leaflets open.
Figure 5:
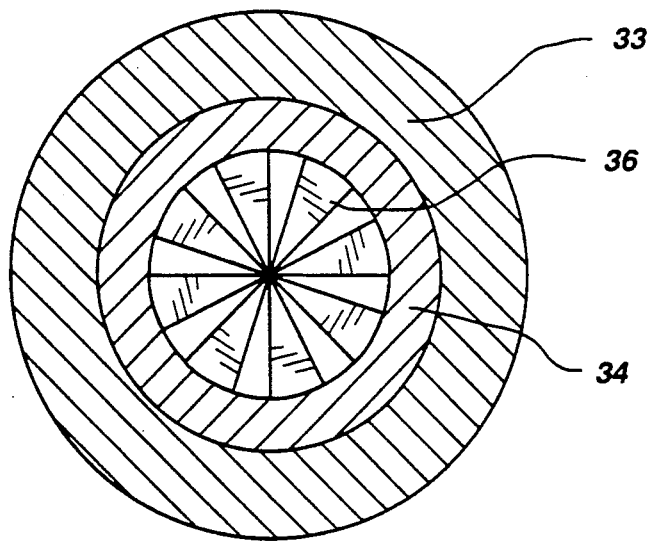
FIG. 5 provides a graphic cross section of a drive motor along the impeller plane which is useful with the proposed invention and capable of being positioned within the septum between the respective ventricles.
Figure 6:
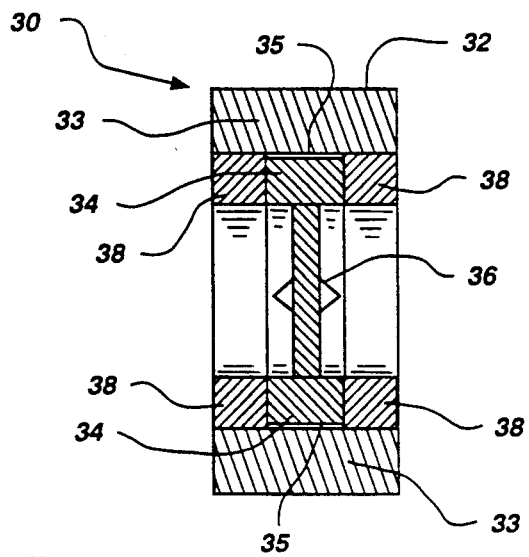
FIG. 6 graphically illustrates a cross section of the drive motor of FIG. 5, rotated 90 degrees to be parallel in orientation to the flow channel.

The upper portion of each ventricle, referred to as the snout, provides structural support for the valved inlets 40 and 43 and outlets 41 and 42 suitable for use in a TAH to enable unidirectional flow of blood through each ventricle in response to pumping action of the pumping membrane. Although many valves are available for implementing the required unidirectional flow, the present inventors have developed an improved valve which provides enhanced response time to directional flow change. This valve is shown in FIG. 3. and comprises a bi-leaflet valve 44 wherein the leaflets 45 and 46 of the bi-leaflet valve are biased to a partially open position to thereby reduce the response time for opening of the valve means in response to blood flow. In the preferred embodiment of this disclosure, the leaflets 45 and 46 of the bi-leaflet valve include polarized magnets 47 and 48 which are positioned on opposing leaflets to create counter magnetic forces which urge the leaflets into a separated, open configuration. The amount of magnetic field is minimal and only need barely urge the respective leaflets to rest in a separated configuration. This slightly open configuration reduces the amount of inertia which the blood flow must overcome to open the valve.

The subject bileaflet valve may be constructed of Isoplast (Trademark) or other stiff polymer material. Each leaflet is encased in a elastomer envelope such as polyurethane, which also serves as a hinge 49 and a hinge 50 on the coaptation line. These leaflets are configured to open completely, so that they are outside the flow path of the bloodstream. As illustrated in the figure, a 40 degree movement is sufficient for this purpose.

In the present TAH configuration traditional tri-semilunar valves are used in the aorta and in the pulmonary artery. Although they have three cusps the valve is sketched as a tricusp valve for clarity's sake. It has been discovered that matching of the properties of the three leaflets of the tricusp semilunar valves can be accomplished by the following unique procedure. Elastomer sheets to be processed through thermo forming are first extruded. Because there is molecular alignment in the direction of extrusion, the physical properties of each sheet are matched along the direction of extrusion. These three sheets are then superimposed along equal, separated orientations of 120 degrees, representing each of the three leaflets of the valve. When the sheets are subjected to the conventional thermo forming process, the respective leaflets are formed from the superimposed sheets to produce leaflets of equal thickness, flexion and identically oriented flex lines.

This process is illustrated in FIGS. 9 and 10, wherein 10 mil sheets of Pellathane 80, 81, 82 were processed to form the tricusp valve 85. These sheets were oriented at 120 degree orientations 90, 91, and 92. The resulting valve 85 formed preserves the respective molecular orientations 90, 91 and 92 with their attendant matched properties. Valve performance for each of the three leaflets was predictably uniform.

Sinus valsalva are provided in the aorta or pulmonary artery and for the inflow valve in the ventricle. Actual placement of the valved inlet and outlet means is well known to those skilled in the art and need not presented in further detail.

A primary feature of the present invention is utilization of a fluid drive motor 30 capable of reversible flow which can be positioned within and circumscribed by the septum 14a of the TAH. This drive motor includes a flow channel 31 which communicates between the respective pumping chambers 17 of the left and right ventricle enclosures. It will be noted that the new positioning of the drive motor within the septum greatly reduces the displacement distance required for the pumping fluid. Use of the septum as a support structure for the drive motor eliminates the need for providing a flow channel for pumping fluid, thereby reducing drag arising from friction generated at the flow channel surface.

The drive motor such as is manufactured by Sierracin/Magnedyne or other companies is generally configured as a round, flat structure with a diameter of 1.94 inches. A housing 32 contains stators on the periphery, with coils 33. An armature 34 and hydrodynamic bearing 35 are supported within the coils, and support the impeller assembly 36. The use of the hydrodynamic bearing 35 substantially eliminates wear within the system and supports the rotating impeller assembly which functions as the flow channel between the respective pumping chambers. A lateral thrust bearing 38 is coupled to the housing 32 and maintains proper position of the impeller assembly within the hydrodynamic bearing.

The armature and the stators of the motor are both imbedded in epoxy with the hydrodynamic bearing 35 in between. To accomplish this, first the exact dimensions of the parts are machined, then molds are made of these parts in room-temperature vulcanizing silicone. Finally the pats of the motor are placed in the molds and the molds are filled with a resin, under vacuum.

As said above the fluids of the hydrodynamic bearing prevents the surfaces from touching and consequently there is no wear. Indeed the inventors have run these hydrodynamic bearings made of aluminum with water as lubricants and reversing as described without visible wear for six months. Epoxy bearings worked equally well. In the unlikely case that the fluid would be drained out the facing surfaces of the bearings are coated with two different polymers with low friction. The motor will be reversed in rotation 40 to 120 times per minute. The motor and impeller speed will be between 6,000 and 12,000 rpms, with greater speed toward the left ventricle than toward the right. The time required to switch from full-speed left to full-speed right will be about 14/1000 of a second. Because the motor will be in constant movement, the film of liquid on the hydrodynamic bearing will stay in tact, protecting the system from wear.

Figure 11:
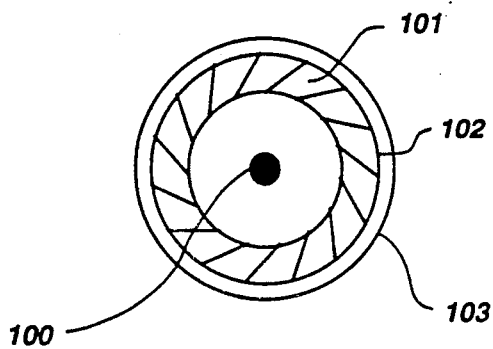
FIG. 11 shows a graphic side view of an alternate motor/impeller design.
Figure 13:
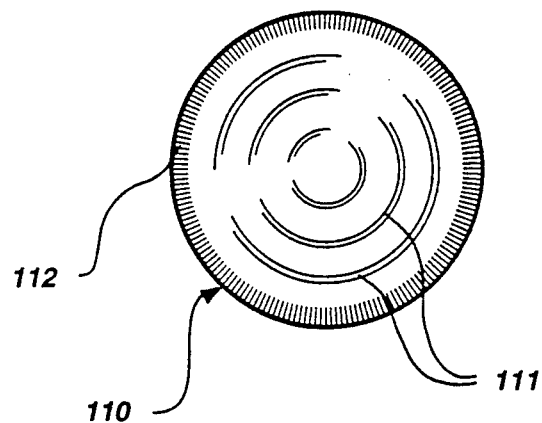
FIG. 13 illustrates a top view of an alternate pumping diaphragm as used in the present invention.

The shroud for the impeller consists of the armature of the motor and has an approximate inner diameter of 1.0 inch. The impeller outer diameter likewise corresponds to the 1.0 inch dimension. There are 16 impeller blades of 0.225 inches in height and length, with a blade thickness of 0.029 inches. Each blade is oriented at 45 degrees to provide maximum driving force in both forward and reverse directions. Although this describes the present impeller system, other configurations are also possible. For example, an alternative motor design is shown in FIG. 11. In this embodiment, the motor 100 is positioned at a central location, with the impeller blades 101 disposed around it. A surrounding shroud provides containment for the motor and impeller blades and is attached to a surrounding housing which contains the hydrodynamic bearing. These motors are also commercially available and fit well within the septum in a manner similar to the flat motor previously described.

Figure 7:
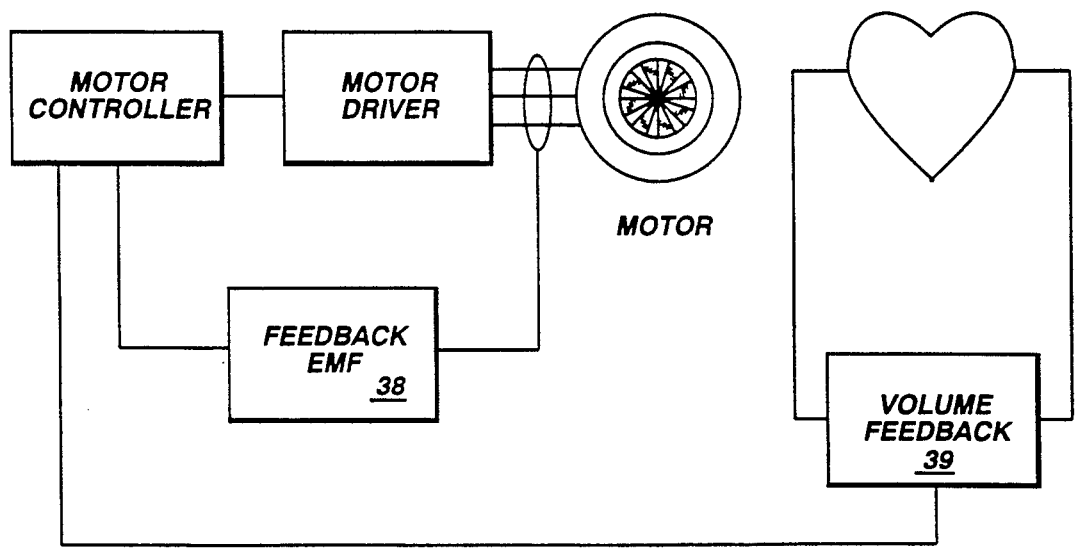
FIG. 7 provides a block diagram of the motor control circuitry which is exemplary of a useful drive system for the present invention.

The motor will be controlled by an implantable box containing the required microcircuitry to operate the continuously reversing drive orientation. An exemplary diagram of this circuitry is shown in FIG. 7. Actual motor drive commands will be generated based on EMF feed back 38 and volume feedback 39. This is similar to the control system used with the Jarvik hydro-electric heart disclosed in the referenced U.S. Patent. Other motor control systems may be applied and are well within the ability of those skilled in the art.

It will be apparent that the transfer of equal volumes of pumping fluid between the pumping chambers of the respective ventricles will generate equal volumes of blood displacement. It is also well known that the volume of blood pumping by the left ventricle in a natural heart is greater than that pumped by the right ventricle. This is partly due to the bronchial circulation which empties into the pulmonary veins. Also, losses by extension under pressure and leaking of valves are greater on the higher pressure left than on the right side. This can be resolved by providing a small extension reservoir for hydraulic fluid on the right side or, by using a soft, inward flexible wall for the right ventricular housing as has been previously mentioned. A soft housing on either side will also help to prevent excessive suction and/or prevent sucking in of the atrial wall during diastole.

The present invention offers numerous advantages over prior art TAH devices. Because it is a single unit, with a self contained drive motor, the total heart function can be placed within the living body, enabling total mobility. If the exterior wall is formed of a deformable, biocompatable polymer material which may be collapsed to a reduced size during implantation, implantation by the surgeon is much easier and less traumatic for surrounding tissue and organs.

Operating efficiencies developed by the improved location of the pumping motor also reduce power requirements, as well as reduction in size. For example, whereas the prior art motors being utilized were as much as 74 mm in length, the current motor is only 7.6 mm. In addition, the weight of the new motor is only 85.7 gms, whereas the prior motors weighed as much as 350 gms. The volume of space taken by prior art motors based on the above factors was approximately 65 cc. The present motor requires only 14.5 cc.

Power is supplied to the drive motor by means of a transcutaneous power supply which transfers electrical power to the fluid drive motor without being in direct, electrical contact therewith. Such systems are now available or are under development and will be commercially available in the near future.

The present invention also discloses the use of an air drive line 60 coupled to each ventricle and being in direct fluid communication with the pumping chamber. Each air drive line includes a distal end (not shown) configured for placement near an epidermal layer of a host patient such that quick access is enabled to the respective air drive lines in the event of failure of the fluid drive motor. Initially, the air drive lines 60 can be used to test the operation of the implanted TAH and insure that the system is totally functional. Once verified, the air lines may be used to fill the pumping chambers with hydraulic fluid for final preparations as an electrohydraulic heart.

Each drive line includes means for sealing its distal end until direct access to the pumping chambers is required. These lines provide excellent conduit for exiting wires or leads attached to the drive motor, thereby avoiding the difficulty of breaching an otherwise sealed TAH housing. These electrical leads may be coupled at one end to the fluid drive motor and extend through at least one of the air drive lines to a subepidermal layer for electromotive interaction with the external, transcutaneous power supply.

In connection with enhancement of blood compatibility of the blood chamber, the present invention provides for improved seamless surface character of the juncture of the blood sac with the housing. This is accomplished by use of radio frequency welding techniques disclosed in combination with the following method of fabrication of the TAH of the present invention. Specifically, this method comprises the steps of:

forming first and second ventricle enclosures of biocompatable polymer in a configuration which enables the respective ventricles as left and right ventricles in the TAH with each ventricle enclosure having an exterior wall formed of (i) contacting wall structure and (ii) noncontacting wall structure which collectively encloses an interior volume comprised of a blood chamber and pumping chamber, said step including the forming of the interior volume by sealing at least one pumping membrane at an interior surface of the exterior wall so as to form a pumping chamber associated with the contacting wall structure and divided from the blood chamber;

joining together the contacting wall structure of each ventricle enclosure in intercontacting relationship with the contacting walls of the respective ventricles forming a septum which structurally separates the pumping chamber of the first ventricle enclosure from the pumping chamber of the second ventricle enclosure;

positioning fluid drive motor capable of reversible flow within the septum, with the fluid drive motor being circumscribed by the septum such that a flow channel through the fluid drive motor communicates between the respective pumping chambers of the first and second ventricles.

The specific method for welding comprises the steps of preparing a conductive metal insert or part for positioning within the ventricle at a place where one or more sections have to be welded together. For example, a conductive piece of metal is made in a configuration which corresponds to the configuration of the final sealed perimeter, such as the juncture of the blood sac with the snout. A metal insert with a flat, smooth perimeter surface which operates as a mandrel for forming the final sealed perimeter as a seamless juncture is then prepared, along with a mating, exterior, conductive metal insert configured with a smooth interior opening which corresponds in shape to the configuration of the smooth perimeter of the first metal insert, but with a slightly larger diameter which leaves a uniform separation gap when inserted around the first metal insert which barely permits capture of the polymer materials to be sealed together therein. The remaining steps comprise:

inserting the first metal insert within the ventricle or snout of the ventricle such that surrounding polymer material to be sealed is tightly drawn across the smooth perimeter of the first metal insert;

positioning additional, surrounding ventricle material to be sealed to the polymer material which is already in position around the first metal insert such that the two materials are in overlapping relationship;

inserting the first metal insert, with associated materials to be sealed, within the mating exterior metal insert such that the materials to be sealed are sandwiched between the opposing smooth faces of the mated metal inserts; and applying a high frequency, alternating current to the respective metal inserts sufficient to generate enough heat to fuse the respective materials sandwiched between the metal inserts into a seamless bond.

By providing a slight taper to the flat, smooth perimeter, and a corresponding slight taper to the smooth interior opening, the first metal insert, having polymer material mounted thereon for sealing, cannot slide through the interior opening of the mating metal insert and the opposing smooth perimeter and interior opening are in approximate parallel orientation. This significantly simplifies the correct adjustment of the two mating members to a proper relationship.

Figure 12:
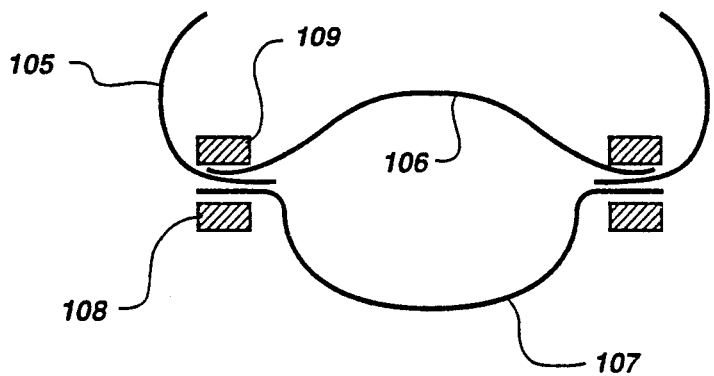
FIG. 12 shows a graphic cross section of an alternate system for radio frequency welding joining edges of a pumping chamber.

This procedures are illustrated by the graphic representation shown in FIG. 8. The first metal insert 70 is placed in the snout 73 of each ventricle, with the polymer material 71 in surrounding orientation. The mating exterior metal insert 72 is configured as a split clamping ring and is positioned around the first metal insert with polymer material which is of a dielectric character. A high frequency of approximately 27 megahertz to 40 megahertz alternating current is applied. The molecules begin to vibrate and produce the required heat to fuse the layers of ventricle and polymer together. The process takes about 20 seconds and produces a virtually seamless surface which greatly reduces likelihood of clotting. The procedure can be adapted to any configuration by merely fabricating the respective metal inserts into appropriate configurations. Rings of differing diameters could be used instead of the illustrated inserts. For example, FIG. 12 shows a graphic cross section of a ventricle housing 105 which is being sealed to the peripheral edge of a diaphragm 106 and a base member 107. The respective peripheral edges of these members are blocked together between opposing rings 108 and 109, which are of brass composition and which are coupled to a radio frequency source. By applying the procedures indicated above and compressing the polymer materials of 105, 106 and 107 between the respective rings 108 and 109, a smooth juncture and seal can be accomplished. This juncture greatly enhances blood compatibility and represents an inexpensive method of manufacture which can greatly reduce the cost of such artificial ventricles.

Other variations will be noted with respect to the metal inserts or rings and which are within the ability of those skilled in the art to adapt to meet particular manufacturing requirements. For example, if the metal insert 70 is too large to be delivered through one of the valve openings at the snout it can be divided in two or more parts which can be disassembled before delivery through the opening.

Figure 2:
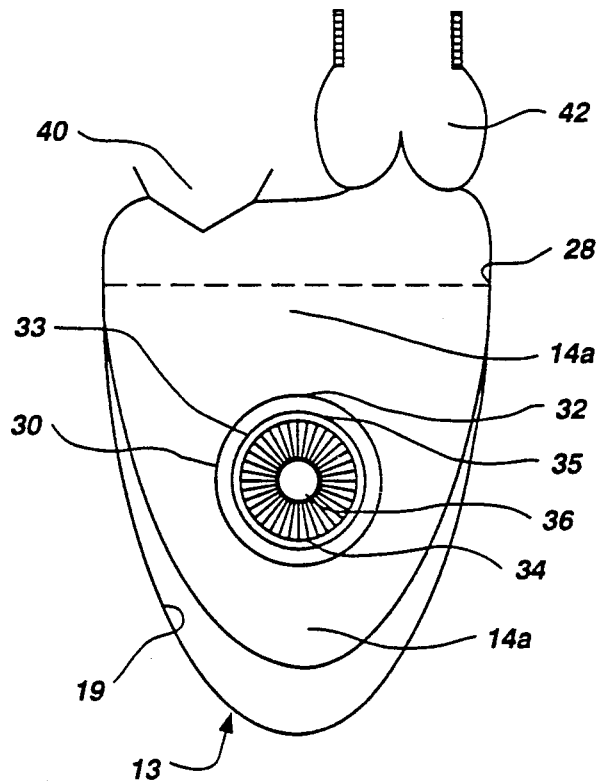
FIG. 2 provides a side view of the graphic illustration of FIG. 1.

It is to be understood that the foregoing description of inventive features is merely exemplary. For example, the blood ports for in and out flow valves as described in connection with FIGS. 1 and 2 may be located directly in the blood chamber, rather than in the snout. Additionally, it has been discovered that the diaphragm configuration, such is shown at item 106 in FIG. 12, may be configured as a corrugated structure having many concentric rings which provide for enhanced extension during pumping action. Hatching marks 112 indicate the location for the RF seal which was applied by the respective rings 108 and 109 of FIG. 12.

Those of ordinary skill in the art will appreciate that numerous additional variations may be made of the specific examples given. Accordingly, the scope the present invention is not to be limited by particular construction or method steps, but only by the following claims.

We claim:

1. A total artificial heart (TAH) for placement inside a living body, said TAH comprising:

first and second ventricle enclosures operable as left and right ventricles in the TAH, each ventricle enclosure having an exterior wall formed of (i) contacting wall structure and (ii) noncontacting wall structure which collectively encloses an interior volume comprised of a block chamber and pumping chamber, said interior volume including at least one pumping membrane sealed at a single, continuous periphery of the pumping membrane at an upper portion of an interior surface of the exterior wall and configured to divide said block chamber from said pumping chamber, said pumping membrane being continuous and uninterrupted within the single, continuous periphery;

said contacting wall structure of each ventricle enclosure being configured for intercontacting relationship wherein the contacting walls of the respective ventricles form a septum which structurally separates the interior volume of the first ventricle enclosure from the interior volume of the second ventricle enclosure;

said noncontacting wall structure comprising the remaining exterior wall of each ventricle enclosure;

said pumping chamber of each ventricle being enclosed by at least a portion of (i) the septum, (ii) the pumping membrane and (iii) any surrounding noncontacting wall structure;

said blood chamber being positioned above the pumping membrane, each blood chamber having valved inlet and outlet means suitable for use in a TAH to enable unidirectional flow of blood through each ventricle in response to pumping action of the pumping membrane;

a single, fluid drive motor capable of reversible flow and being positioned within and circumscribed by the septum and including a flow channel therethrough which communicates between the respective pumping chambers of the first and second ventricle enclosures;

powering means for driving the fluid drive motor; and a fluid medium contained within the pumping chambers and being responsive to the fluid drive motor to be reversibly transferred between the pumping chambers of the first and second ventricle enclosures and to reversibly extend and retract the continuous pumping membrane to enlarge and contract the blood chamber and thereby simulate natural pumping action of a natural heart.

2. A TAH as defined in claim 1, wherein the exterior wall is formed of a deformable, biocompatable polymer material which may be collapsed to a reduced size during implantation of the TAH.

3. A TAH as defined in claim 1, wherein the fluid drive motor comprises a disk shaped motor with a centrally located impeller assembly positioned within the flow channel and plane of the septum and being capable of bidirectional, rotational movement to facilitate reversible flow of the fluid medium.

4. A TAH as defined in claim 3, wherein the impeller assembly is supported at its perimeter by a hydrodynamic bearing, said impeller assembly being magnetically actuated by a circumscribing or centrally located armature and electrical stator.

5. A TAH as defined in claim 1, wherein said powering means comprises a transcutaneous power supply which transfers electrical power to the fluid drive motor without being in direct, electrical contact therewith.

6. A TAH as defined in claim 1, further comprising an air drive line coupled to each ventricle and being in direct fluid communication with the pumping chamber, each air drive line having a distal end configured for placement near and under the skin of a host patient such that quick access is enabled to the respective air drive lines in the event of failure of the fluid drive motor, each drive line including means for sealing its distal end until direct access to the pumping chambers is required.

7. A TAH as defined in claim 6, wherein the powering means for the fluid drive motor includes electrical leads coupled at one end to the fluid drive motor and extending through at least one of the air drive lines to a subdermal layer for electromotive interaction with the external power supply.

8. A TAH as defined in claim 1, wherein each ventricle comprises a single blood sac which defines the blood chamber and also operates as the pumping membrane, said blood sac having a snout which includes the inflow and outflow valves for transfer of blood to and from the blood chamber, said pumping chamber being defined by the single blood sac which operates concurrently as the pumping membrane on a lower end and forms an exterior wall extension of the housing member at an upper end, said blood sac being configured for partial positioning at the lower end within the housing member and being sealed with the housing member to enclose and seal the pumping chamber within the housing, except for the flow channel through the drive motor and septum.

9. A TAH as defined in claim 8, wherein the external wall is substantially comprised of the housing member which defines a large, interior pumping chamber into which the blood sac is inserted, forming a blood chamber which is substantially surrounded on at least one side by the pumping chamber.

10. A TAH as defined in claim 9, wherein the septum is formed by the housing wall which encloses a portion of the pumping chamber, said septum and housing wall having the fluid drive motor positioned therein for transfer of drive fluid between the respective ventricle pumping chambers.

11. A TAH as defined in claim 8, wherein the blood sac is comprised of at least two layers of elastomer, each sheet having a thickness of less than 0.020 inches, said layers including a dispersion of lubricant therebetween.

12. A TAH as defined in claim 1, wherein the valved inlet and outlet means include at least one bi-leaflet valve wherein the leaflet of the bi-leaflet valve are biased to a partially open position to thereby reduce the response time to valve opening in response to blood flow.

13. A TAH as defined in claim 12, wherein the respective leaflets of the bi-leaflet valve include polarized magnet means positioned thereon of common polarity with sufficient magnetic field strength to barely urge the respective leaflets to rest in a separated configuration.

14. A TAH as defined in claim 1, wherein the attachment of the various walls and membranes is substantially seamless to reduce occurrence of clotting and other adverse blood conditions.

* * * * *